(12) United States Patent
Crabb et al.

(10) Patent No.: US 12,343,191 B2
(45) Date of Patent: Jul. 1, 2025

(54) MEDICAL IMAGE SYNTHESIS FOR MOTION CORRECTION USING GENERATIVE ADVERSARIAL NETWORKS

(71) Applicant: University of Utah Research Foundation, Salt Lake City, UT (US)

(72) Inventors: Brendan Thomas Crabb, Salt Lake City, UT (US); Frederic Nicolas Firmin Noo, Midvale, UT (US); Gabriel Chaim Fine, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 416 days.

(21) Appl. No.: 17/781,037

(22) PCT Filed: Dec. 1, 2020

(86) PCT No.: PCT/US2020/062699
§ 371 (c)(1),
(2) Date: May 30, 2022

(87) PCT Pub. No.: WO2021/113235
PCT Pub. Date: Jun. 10, 2021

(65) Prior Publication Data
US 2022/0409161 A1    Dec. 29, 2022

Related U.S. Application Data

(60) Provisional application No. 63/085,491, filed on Sep. 30, 2020, provisional application No. 62/942,675, filed on Dec. 2, 2019.

(51) Int. Cl.
*A61B 6/00* (2024.01)
*G06V 10/32* (2022.01)
(Continued)

(52) U.S. Cl.
CPC ............ *A61B 6/5264* (2013.01); *G06V 10/32* (2022.01); *G06V 10/454* (2022.01); *G06V 10/82* (2022.01); *G06V 2201/03* (2022.01)

(58) Field of Classification Search
CPC .... A61B 6/5264; G06V 10/454; G06V 10/32; G06V 10/82
See application file for complete search history.

(56) References Cited

U.S. PATENT DOCUMENTS 6,819,790 B2   11/2004   Suzuki et al.
8,897,527 B2   11/2014   Star-lack et al.
(Continued)

FOREIGN PATENT DOCUMENTS

WO    2019/147767 A1    8/2019

OTHER PUBLICATIONS

Gao et al., "Deep learning-based digital subtraction angiography image generation," International Journal of Computer Assisted Radiology and Surgery, vol. 14, (2019), pp. 1775-1784.
(Continued)

*Primary Examiner* — David Bilodeau
(74) *Attorney, Agent, or Firm* — Workman Nydegger

(57) ABSTRACT

A computer system is configured to remove motion artifacts in medical images using a generative adversarial network (GAN). The computer system instantiates the GAN having one or more generative network(s) and one or more discriminative network(s) that are pitted against each other to train a generative model and a discriminative model. The training uses a training dataset including a plurality of medical images that are previously classified as without significant motion artifacts for diagnostic purposes. The discriminative model is trained to classify medical images as real or artificial. The generative model is trained to enhance the quality of a medical image and remove motion artifacts by producing a medical image directly from a post-contrast image, without using a pre-contrast mask.

20 Claims, 7 Drawing Sheets

(51) Int. Cl.
*G06V 10/44* (2022.01)
*G06V 10/82* (2022.01)

(56) References Cited

U.S. PATENT DOCUMENTS

| | | | | |
|---|---|---|---|---|
| 10,242,292 | B2* | 3/2019 | Zisimopoulos | G06N 3/045 |
| 11,475,351 | B2* | 10/2022 | Luo | G06V 10/82 |
| 2007/0036431 | A1* | 2/2007 | Terakawa | G06F 18/214 |
| | | | | 382/118 |
| 2008/0051648 | A1 | 2/2008 | Suri et al. | |
| 2019/0147588 | A1 | 5/2019 | Rowley Grant et al. | |
| 2019/0333219 | A1 | 10/2019 | Xu et al. | |
| 2020/0134876 | A1* | 4/2020 | Park | G06F 18/214 |
| 2020/0160535 | A1* | 5/2020 | Ali Akbarian | G06N 5/046 |

OTHER PUBLICATIONS

Greenspan et al., "Guest editorial deep learning in medical imaging: Overview and future promise of an exciting new technique," IEEE Transactions on Medical Imaging, vol. 35, No. 5, (2016), pp. 1153-1159.

International Search Report and Written Opinion received for PCT Patent Application No. PCT/US2020/062699, mailed on Mar. 4, 2021, 10 pages.

Jacobs et al., "Effects of Transfer Learning on Data Augmentation With Genrative Adversarial Networks", in ScienceDirect [online], pp. 426-431, published Sep. 16, 2019.

Long et al., "Fully convolutional networks for semantic segmentation," Proceedings of the IEEE conference on computer vision and pattern recognition, (2015), pp. 3431-3440.

Sundarapandian et al., "DSA image registration using non-uniform MRF model and pivotal control points," Computerized medical imaging and graphics, vol. 37, (2013), pp. 323-336.

Wang et al., "Augmenting Vascular Disease Diagnosis by Vasculature-aware Unsupervised Learning," bioRxiv (2020), 33 pages.

Wolterink et al., "Generative adversarial networks for noise reduction in low-dose CT," IEEE transactions on medical imaging, vol. 36, No. 12, (2017), pp. 2536-2545.

Zhang et al., "DSA Image Registration Based on 30 Space-Time Detection", in KTH Royal 1-20 Institute of Technology [online], pp. 1-49 published 2010 [retrieved on Jan. 23, 2021.

Hong et al., "How Generative Adversarial Networks and Their Variants Work: An Overview", Feb. 28, 2019, pp. 1-41.

Kazeminia et al., "GANs for medical image analysis", Artificial Intelligence in Medicine, vol. 109, Aug. 9, 2020, 101938, pp. 1-19.

Ronneberger et al., "U-Net: Convolutional Networks for Biomedical Image Segmentation", Oct. 5, 2015, Advances in Biometrics : International Conference, ICB, Seoul, Korea, Aug. 27, 2009, pp. 8.

* cited by examiner

MEDICAL IMAGE SYNTHESIS FOR MOTION CORRECTION USING GENERATIVE ADVERSARIAL NETWORKS

CROSS-REFERENCE TO RELATED APPLICATIONS

This patent application is a nationalization of and claims priority to PCT Application No. PCT/US2020/062699 filed on Dec. 1, 2020 and entitled MEDICAL IMAGE SYNTHESIS FOR MOTION CORRECTION USING GENERATIVE ADVERSARIAL NETWORKS, which claims the benefit of and priority to U.S. Provisional Patent Application No. 63/085,491 filed Sep. 30, 2020 and entitled "IMAGE SYNTHESIS FOR MOTION CORRECTION IN DIGITAL SUBTRACTION ANGIOGRAPHY USING GENERATIVE ADVERSARIAL NETWORKS" and claims the benefit of and priority to U.S. Provisional Patent Application No. 62/942,675 filed Dec. 2, 2019 and entitled "MOTION CORRECTION IN DIGITAL SUBTRACTION ANGIOGRAPHY". Each of the aforementioned applications is incorporated by reference herein in their entirety.

BACKGROUND

Computers and computing systems have affected nearly every aspect of modern living. Computers are generally involved in work, recreation, healthcare, transportation, entertainment, household management, etc. For example, healthcare has seen an increasingly growing presence of computers and computing systems being integrated into patient care. Whereas previously computers were used primarily as a records and billing management platform, due to advances in Artificial Intelligence (AI) and image processing, computers are more frequently being used to analyze patient test results and images in order to identify problems and/or aid a medical practitioner in identifying the problems.

In particular, medical imaging refers to techniques and processes used to create images of various parts of the human body for diagnostic and treatment purposes within digital health, including (but not limited to) X-ray radiography, Fluoroscopy, Computed Tomography (CT), ultrasound, nuclear medicine imaging techniques, and Magnetic Resonance Imaging (MRI). During imaging acquisition, a patient is often required to refrain from moving. Otherwise, motion artifacts would occur, which may appear as blurring, streaking, or shading on the acquired medical image.

For example, digital subtraction angiography (DSA) is a commonly used method for the visualization of vasculature throughout the human body whereby a sequence of 2D digital x-ray images are created to show the passage of injected contrast material through the vasculature. These images are obtained by subtracting a pre-contrast image from subsequent images acquired once the injected contrast has been introduced into the vasculature. Unfortunately, patient motion can render background subtraction difficult, limiting the images' diagnostic quality. As a result, the procedure is often repeated, leading to increased healthcare costs, procedure times, radiation dose, and contrast use.

Conventional methods of reducing the effects of patient motion possess several critical limitations, such as the need for manual input or significant computational requirements, preventing real-time motion correction. Furthermore, these approaches struggle to correct the non-translational motion present in visceral angiograms and frequently generate new artifacts that obscure the vasculature of interest.

Accordingly, there is a need in the art for technical solutions to the current shortcomings and inefficiencies in the field.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Disclosed embodiments include a computer system for removing motion artifacts in medical images using a generative adversarial network (GAN). The computer system is configured to instantiate the GAN having one or more generative network(s) and one or more discriminative network(s). The generative network(s) and the discriminative network(s) are pitted against each other to train a generative model and a discriminative model. The training of the generative network(s) and the discriminative network(s) uses a training dataset including a first plurality of medical images that are previously classified as without significant motion artifacts for diagnostic purposes. For example, the first plurality of medical images may be cerebral images generated by digital subtraction angiography (DSA) and confirmed by human experts as without significant motion artifacts.

In some embodiments, for each of the first plurality of medical images, when the medical image is not within a predetermined size, the computer system transforms the image into one or more images of the predetermined size (e.g., 256×256), and uses the transformed images with the predetermined size as the training data. For example, when a medical image is larger than the predetermined size, the medical image is split into multiple images having the predetermined size.

The discriminative model is trained to classify digital medical images as with or without significant motion artifacts. The generative model is trained to enhance quality of a medical image to substantially remove motion artifacts in the medical image. When the computer system receives a new medical image having significant motion artifacts, the computer system enhances the quality of the new medical image by the generative model, such that the discriminative model classifies the enhanced medical image as without significant motion artifacts.

In some embodiments, when the new medical image is received, the computer system causes the discriminative model to determine whether the medical image has significant motion artifacts. In response to the determination of having significant motion artifacts, the computer system causes the generative model to enhance the first medical image by substantially removing the motion artifacts in the medical image.

For example, in some embodiments, the new medical image is a medical image generated by DSA having significant motion artifacts, and the computer system causes the generative model to enhance the quality of the medical image by substantially removing the motion artifacts, such that the discriminative model classifies the enhanced image as an image generated by DSA technique without significant motion artifact. In some other embodiments, the new medical image is a contrast image prior to subtraction of a pre-contrast image. The computer system causes the generative model to enhance the contrast image without having to subtract a pre-contrast image, such that the discriminative model classifies the enhanced image as an image generated by DSA technique without significant motion artifact.

In some embodiments, the computer system is further configured to modify the discriminative model and generative model by transfer learning. The transfer learning includes continuing to train the previously trained discriminative model and the generative model using a second plurality of medical images. The second plurality of medical images are also previously classified as without significant motion artifacts. For example, the first plurality of medical images may be cerebral DSA images, and the second plurality of medical images may be hepatic DSA images. Transfer learning allows the computer system to utilize the knowledge gained from the first plurality of medical images to quickly gain additional knowledge from the second plurality of medical images.

Further, in embodiments, each of the one or more discriminative network(s) is a convolutional network that has a receptive field having a predetermined size. In some embodiments, the receptive field of each of the convolutional network(s) is selected from 1×1, 70×70, or 286×286. In some embodiments, at least one of the convolutional network(s) includes U-Net convolutional network(s).

In some embodiments, the GAN has an objective represented by an objective function. The discriminative network(s) is configured to maximize the objective; and the generative network(s) is configured to minimize the objective. In some embodiments, the objective includes a distance loss. In some embodiments, the objective includes a distance loss plus an adversarial loss.

In some embodiments, the GAN is one of the following: (1) pixelGAN, (2) patchGAN, or (3) image GAN. When the GAN is a patchGAN, the discriminative network classifies a digital medical image as having the sufficiently high quality when each patch having a predetermined size in the digital medical image is without significant motion artifacts.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings.

DETAILED DESCRIPTION

Motion artifact is a patient-based artifact that occurs with voluntary or involuntary patient movement during medical image acquisition. When motion artifacts occur, the acquired medical image would appear with blurring, streaking, or shading. Disclosed embodiments provide a solution for the problems caused by motion artifacts using a generative adversarial network (GAN). GANs are generative models that are trained using an adversarial process, in which two models pitted against each other in a minmax two-player game are trained simultaneously. These two models consist of a generative model G that learns the data distribution and a discriminative model D that attempts to discern between samples generated by G and samples in the training dataset. As training progresses, G maximizes the probability of D making a mistake by producing samples indistinguishable from the training data. Disclosed embodiments include a method that leverages the power of GANs to produce enhanced medical images, substantially removing motion artifacts.

Figure 2:
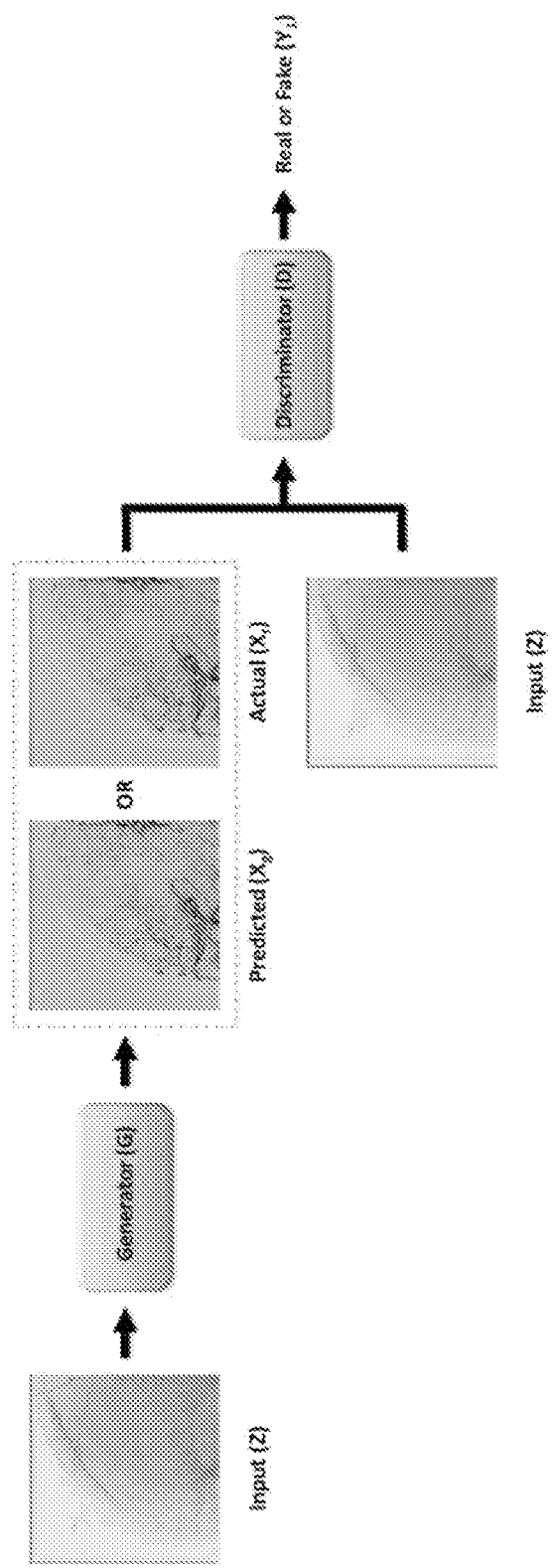
FIG. 2 illustrates a general conditional GAN architecture with a generator (G) and discriminator (D).

FIG. 2 illustrates a schematic diagrams of an example GAN. As illustrated, the GAN includes a generative network (also referred to as generator) G and a discriminative network (also referred to as discriminator) D. As training progresses, G maximizes the probability of D making a mistake by producing images indistinguishable from the training data (i.e., the good medical images). Over several rounds of training, the generator becomes better at producing images that are similar to the good medical images. At the same time, the discriminator improves its capacity for discerning the images generated by G and the good medical images in the training datasetIn so doing, both models become more and more specialized at their respective tasks. Eventually, this adversarial interplay can reach a point where the generator is capable of enhancing images that have significant motion artifacts, and the enhanced images are sufficiently close to the good medical images in the training dataset not only to the discriminator network but also to the human visual interpretation. As such, the disclosed embodiments effectively mitigate the problem caused by the motion artifacts produced by patient motion.

The inventors have performed extensive experiments on real medical images to prove that the principles described herein produce the result as intended. For example, the inventors used DSA images as training and testing data to train a generator G and a discriminator D. The trained generator G not only can effectively enhance DSA images that have significant motion artifacts, but also enhance post-contrast images prior to subtraction of the mask image, eliminating the step of subtraction of mask image.

Digital subtraction angiography (DSA) is a fluoroscopic technique used extensively in angiography for visualizing blood vessels. Radiopaque structures such as bones are subtracted digitally from the image, thus allowing for an accurate depiction of the blood vessels. In particular, a non-contrast image (also referred to as a mask image) of a region is first taken before injecting contrast material and therefore shows only anatomy, as well as any radiopaque foreign bodies (such as surgical clips, stents, etc.) as would be seen in a regular x-ray image. Next, one or more contrast images are taken in succession while contrast material is being injected. These contrast images show the opacified vessels superimposed on the anatomy. The mask image is then subtracted from the contrast images pixel by pixel. The resulting subtraction images should show the vessels only. In some cases, recording can continue to provide a sequence of subtracted images based on the initial mask.

Figure 1:
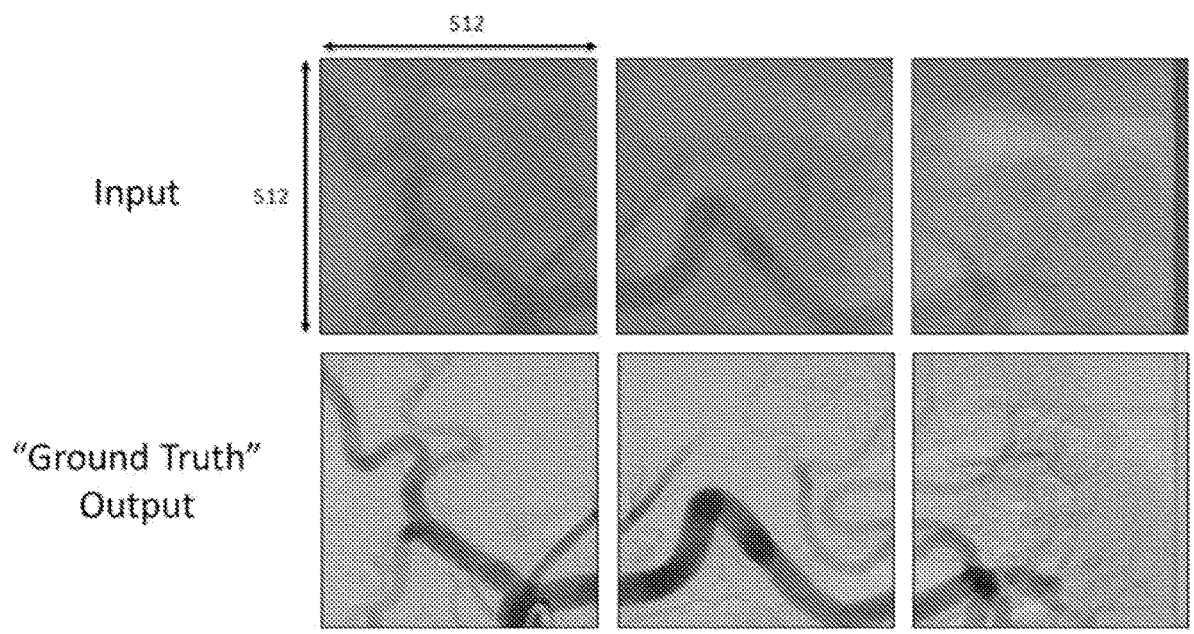
FIG. 1 illustrates native fluoroscopic image patches with injected contrast (512×512 pixels) used as inputs to the neural network during training and the corresponding DSA patches used as ground-truth outputs during training.

FIG. 1 illustrates an example set of contrast images and corresponding subtracted images. The three images in the top row of FIG. 1 are original contrast images before the DSA process, and the three images in the bottom row of FIG. 1 are the images after the DSA process. Hereinafter, the images after the DSA process are also called DSA images. As illustrated, the DSA images in the bottom row show the vessels much more clearly than the original contrast images in the top row.

Notably, to obtain clear DSA images, the patient must lie still between the acquisition of the mask image and the subsequent acquisition of the contrast image. Otherwise, misregistration of images would occur. Existing solutions for mitigating the movement of the patients includes pixel shifting (either manual or automatic), i.e., moving the mask image retrospectively. Although pixel shifting can correct some of the misregistration of images, certain problems caused by focal movement such as bowel peristalsis often cannot be corrected by pixel shifting.

In an embodiment example, a system is trained to enhance DSA images. The system utilizes three datasets as training datasets that will be referred to as dataset A, B, and C respectively. For all three datasets in this example, imaging studies were generated using Artis angiography systems manufactured by Siemens Healthcare at the University of Utah Hospital or the Huntsman Cancer Institute and were identified and selected using Nuance mPower Clinical Analytics and the University of Utah's NUMAstore PACS system. For all datasets, the presence or absence of motion artifacts was assessed by a human expert.

In the example embodiment, dataset A consists of DSA images of the carotid and cerebral vasculature with minimal or no motion artifacts. Patients were identified by searching mPower for the phrase 'Cerebral Angiogram "general anesthesia"'. Imaging studies for patients meeting this criterion were anonymized and exported as DICOM files for the inclusion in our research. Due to the rigidity of the skull and the administration of general anesthesia, these cerebral angiograms were considered to be the ideal representations of DSA images without motion artifacts. 35 patients (14 males, 21 females) were identified that met this criterion, for a total of 400 series and 7,958 DSA images. Patients in this dataset have a median age of 57 years [range 24-77 years] and a median body mass index (BMI) of 28.38 kg/m² [range 16.14-43.86 kg/m²].

In the example embodiment, dataset B consists of DSA images of the hepatic vasculature with minimal or no motion artifacts. Patients were identified by searching mPower for the phrase 'IR Visceral Angio "hepatic"'. Imaging studies for patients meeting this criterion were anonymized and exported as DICOM files for the inclusion in our research. Thirty-one patients (19 males, 12 females) were identified that met this criterion, for a total of 74 series and 1,203 DSA images. Patients in the dataset have a median age of 59 years [range 18-77 years] and a median body mass index (BMI) of 26.30 kg/m² [range 19.60-52.80 kg/m²].

In the example embodiment, dataset C consisted of visceral DSA images with significant motion artifacts. Patients were identified by searching mPower for the phrase 'IR Visceral Angio'. Imaging studies for patients meeting this criterion were completely anonymized and exported as DICOM files for the inclusion in our research. Twenty-two individual patients (14 males, 8 females) were identified that met this criterion, for a total of 130 series and 3,322 DSA images. Patients in the dataset have a median age of 62 years [range 40-79 years] and a median body mass index (BMI) of 28.32 kg/m² [range 14.84-40.45 kg/m²].

FIG. 1 illustrates native fluoroscopic image patches with injected contrast (512×512 pixels) used as inputs to the neural network during training and the corresponding DSA patches used as ground-truth outputs during training. The datasets A and B consist of training image pairs, with the original native fluoroscopic image with injected contrast as the input and the DSA without motion artifacts as a ground truth output. An example of these training pairs can be seen in FIG. 1. Datasets A and B were randomly split into training, testing, and validation datasets using an 80-10-10 percent split. During this split, images from the same x-ray series were confined to the same dataset. Additionally, the original images, which were frequently 1024×1024 pixels or larger, were split into 512×512 pixel patches. As a result, dataset A produced a total of 23,784 training images, 2,912 validation images, and 2,960 testing images. Dataset B produced a total of 5,065 training images, 503 validation images, and 775 testing images.

Conditional adversarial networks excel on large datasets of aligned image pairs, such as the input and output pairs in datasets A and B. These architectures consist of two distinct neural networks: a generator (G) and discriminator (D). As shown in FIG. 2, the generator is used to generate the output images ($X_g$) from the input (Z). The discriminator attempts to discern real images ($X_r$) in the training data from artificially generated images ($X_g$), producing a classification of real or fake ($Y_1$). Using this process, the generator progressively produces more accurate and realistic images as the discriminator gets more adept at distinguishing between artificial and real DSA images.

In at least one embodiment, the disclosed system utilizes the pix2pix architecture as a conditional GAN. The pix2pix architecture further utilizes the neural network Unet as the generator. Unet is an encoder-decoder with skip connections between mirrored layers in the encoder and decoder stacks. As such, in at least one embodiment, the system uses the Unet as the generator for the network; however, one will appreciate that several different architectures may be used for the discriminator network.

The performance of Unet in combination with three different discriminator architectures was investigated. The primary discriminator architecture was part of the original pix2pix implementation. This discriminator focuses on local image patches and attempts to classify each N×N patch in an image as real or fake. The algorithm was then run convolutionally across the image, averaging responses to produce an ultimate classification of real or fake. As a result, this discriminator assumes independence between pixels separated by N and effectively models the image as a Markov random field.

Three distinct discriminators were implemented by varying the size of the discriminator receptive field. The first discriminator, termed PixelGAN, uses a receptive field size of 1×1 and has been shown to improve color histogram matching in generated results. The second discriminator, termed PatchGAN, uses a receptive field size of 70×70. Finally, the third discriminator, termed ImageGAN, uses a receptive field size of 286×286. A summary of these architectures can be seen in Table 1.

TABLE 1

Network Architectures and Objective Functions.

| Method | Discriminator Receptive Field Size (N × N) | Objective Function |
| --- | --- | --- |
| Unet | | L1 |
| Unet + PixelGAN | 1 × 1 | L1 + Adversarial Loss |
| Unet + PatchGAN | 70 × 70 | L1 + Adversarial Loss |
| Unet + ImageGAN | 286 × 286 | L1 + Adversarial Loss |

In at least one embodiment, the objective function of a conditional GAN can be expressed as, $$L_{CGAN}(G,D)=E_{x,y}[\log D(x,y)]+E_{x,z}[\log(1-D(x,G(x,z)))],$$

where the adversarial discriminator, D, tries to maximize the objective and the generator, G, tries to minimize it. This term is described as the adversarial loss; however, it is also paired with a more traditional L1 distance loss function defined as, $$L_{L1}(G)=E_{x,y,z}[\|Y-G(x,z)\|_1].$$

Consequently, the final objective function can be expressed as, $$G^* = \arg\min_G \max_D L_{cGAN}(G, D) + \lambda L_{L1}(G),$$

where $\lambda$ is a weight term applied to balance the adversarial and L1 losses. Unless otherwise specified, this objective function was used for all training.

To improve the generalizability of the algorithm, extensive data augmentations were utilized during training. Augmentations included random padding and cropping, random contrast adjustments, and random brightness adjustments. Furthermore, horizontal mirroring augmentations were applied to the cerebral angiograms (dataset A) due to the highly symmetric nature of the cerebral vasculature.

Figure 3:
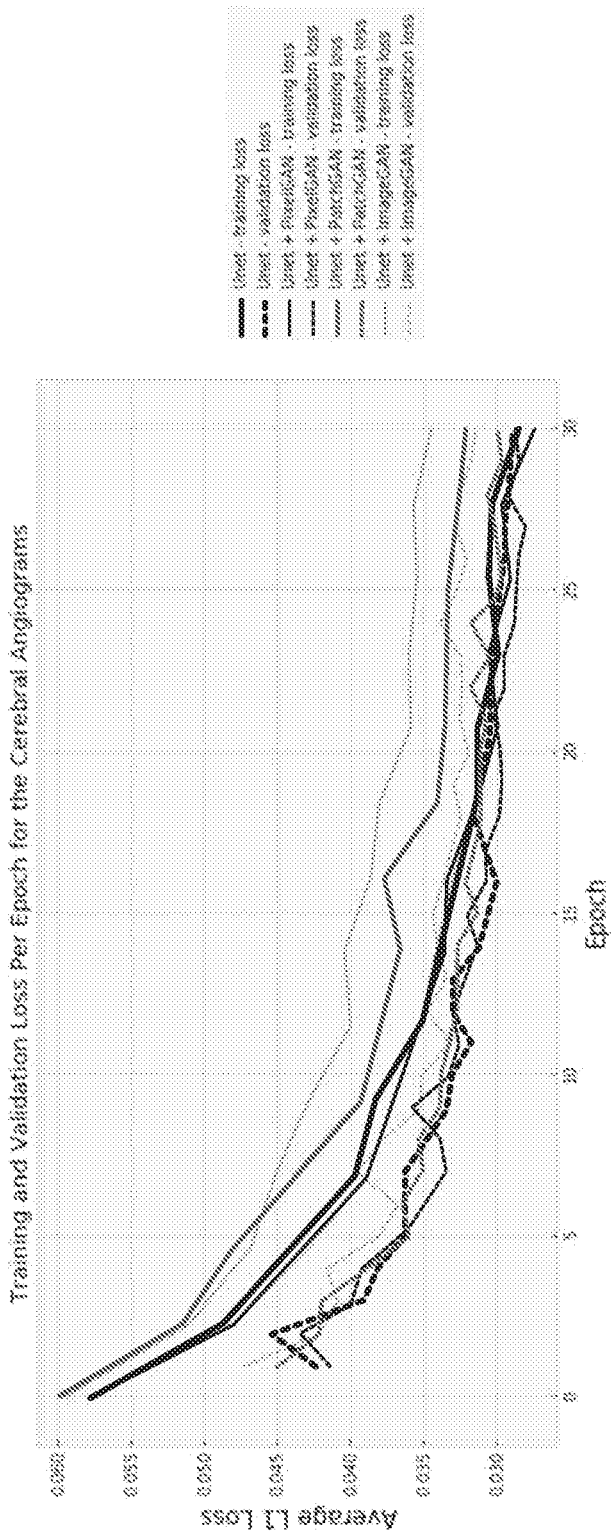
FIG. 3 illustrates training and validation loss curves for each algorithm combination training on the cerebral DSA images (dataset A).
Figure 4:
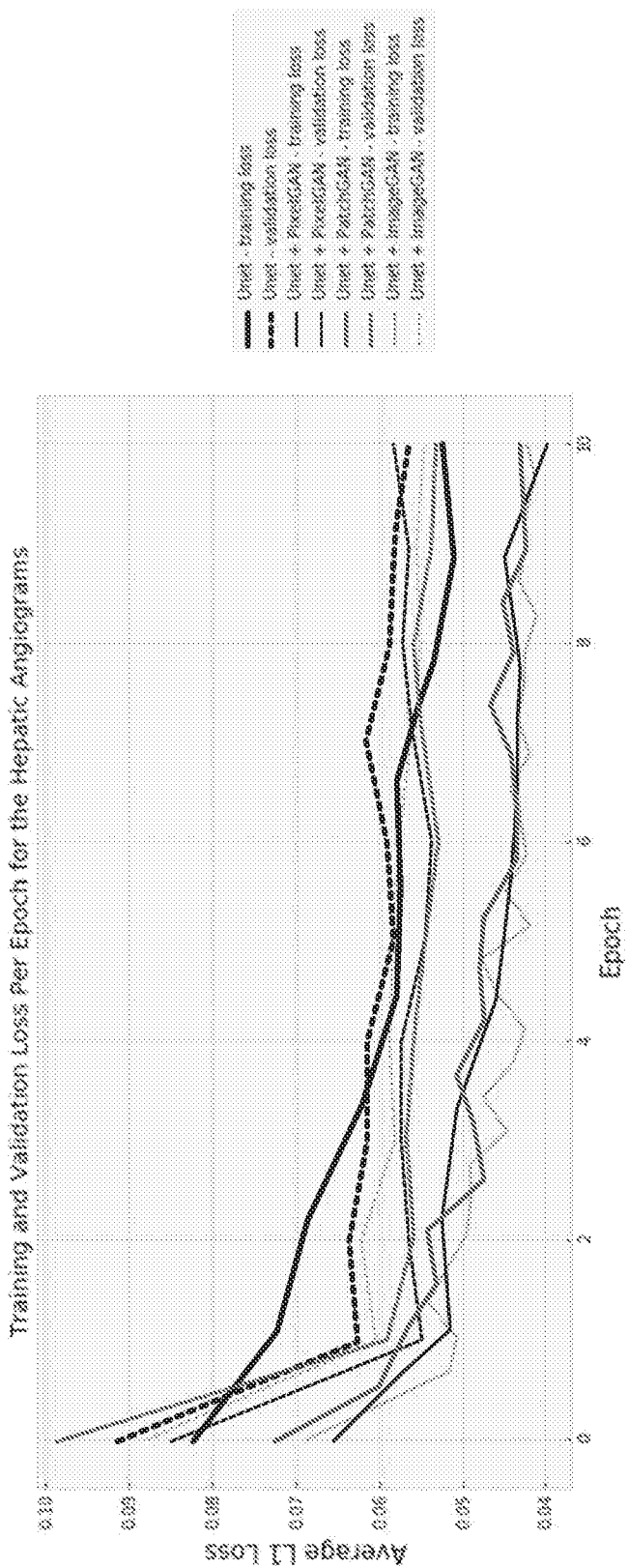
FIG. 4 illustrates training and validation loss curves for each algorithm combination training on the hepatic DSA images (dataset B).

Training was started on dataset A, using random weight initialization, and performed for a total of 30 epochs. Progress was tracked using an L1 loss on the validation dataset and a visual review of the generated DSA images. After training was complete, the algorithm was implemented on the testing dataset and results were manually reviewed (e.g., reviewed by an expert or a board-certified radiologist). Next, using the pretrained weights from dataset A, fine tuning was performed on dataset B for a total of 10 epochs. Progress was tracked using an L1 loss on the validation dataset and a visual review of the generated DSA images. Validation and training loss curves for training on datasets A (cerebral angiograms) and B (hepatic angiograms) can be seen in FIGS. 3 and 4 respectively. More specifically, FIG. 3 illustrates training and validation loss curves for each algorithm combination training on the cerebral DSA images (dataset A), and FIG. 4 illustrates training and validation loss curves for each algorithm combination training on the hepatic DSA images (dataset B).

Furthermore, to assess the utility of transfer learning for this application, the network Unet+PatchGAN was trained on dataset B, with and without transfer learning from dataset A. In this comparison, all training parameters were kept identical other than the initial weights. All training was performed on a machine with two Nvidia GTX Titan GPUs using the Torch machine learning framework and Adam optimization, with an initial learning rate of 0.0002, batch size of 1, momentum $\beta_1$ of 0.5, and $\lambda$ of 200.

To evaluate the performance of the proposed methods, the disclosed methods were used to generate outputs using both a quantitative assessment and a qualitative assessment. The quantitative assessment is accomplished by using the testing datasets, which were not included in the training phase, for both datasets A and B. Since these datasets do not contain any motion artifacts, the algorithm outputs can be compared directly to the ground truth DSA images using a variety of full-reference image quality metrics. This quantitative comparison was used to ensure the ability of each algorithm to accurately reproduce the traditional DSA method in settings without motion artifacts. Furthermore, a quantitative comparison was used to analyze the impact of transfer learning from cerebral angiograms, prior to training on the smaller dataset of hepatic angiograms. Results were compared using a two-sided T-test assuming equal population variances.

The qualitative assessment is accomplished by performing a visual review and comparison of generated images to the ground truth. This step is critical, since image quality metrics often fail to measure clinically relevant features, such as the anatomic accuracy of the vasculature in the generated image. A qualitative assessment was also used to assess the ability of the proposed methods to correct misalignment artifacts in Dataset C, which contains visceral angiograms with significant motion artifacts. Furthermore, this visual comparison was used to determine which algorithm most accurately reproduced the vasculature of interest while also eliminating motion artifacts. Note, even though in embodiments, a qualitative assessment is implemented, there are possible cases that quantitative assessment alone is sufficient.

When performing the quantitative assessment, the visual quality of the generated images for the cerebral and hepatic angiograms was assessed using full-reference image quality metrics, including the mean-squared error (MSE) calculated from normalized images, the structural similarity index (SSIM), and peak signal-to-noise ratio (PSNR). As shown in Table 2 and 3, generated images were visually similar to the ground truth with adequate MSE, SSIM, and PSNR scores for both the cerebral and hepatic angiograms. More specifically, Table 2 depicts Full-Reference (FR) Image Quality metrics, including MSE, SSIM, and PSNR values, for each algorithm combination for the cerebral testing dataset with no motion artifacts present. Generated images were compared directly to the traditional DSA method for visual similarity in the setting of no motion artifacts. Reported as mean value and 95% confidence interval. Table 3 depicts Full-Reference (FR) Image Quality metrics, including MSE, SSIM, and PSNR values, for each algorithm combination for the hepatic testing dataset with no motion artifacts present. Generated images were compared directly to the traditional DSA method for visual similarity in the setting of no motion artifacts. Reported as mean value and 95% confidence interval.

Each proposed method is able to accurately reproduce the traditional DSA method in settings without motion artifacts; this performance was additionally aided by transfer learning from the large dataset of cerebral angiograms. As shown in Table 4, transfer learning significantly improved the MSE, SSIM, and PSNR values of generated images for the testing dataset of hepatic angiograms. More specifically, Table 4 depicts Full-Reference (FR) Image Quality metrics, including MSE, SSIM, and PSNR values, for the Unet+PatchGAN algorithm trained and evaluated on the hepatic angiograms, with and without transfer learning from the cerebral angiograms. Generated images were compared directly to the traditional DSA method for visual similarity in the setting of no motion artifacts. Reported as mean value and 95% confidence interval.

TABLE 2

Full-Reference (FR) Image Quality metrics

Cerebral Angiograms (Dataset A)

| Method | MSE | SSIM | PSNR |
|---|---|---|---|
| Unet | 0.00183 (0.00172 to 0.00194) | 0.880 (0.878 to 0.882) | 30.25 (30.06 to 30.43) |
| Unet + PixelGAN | 0.00181 (0.00169 to 0.00193) | 0.880 (0.878 to 0.882) | 30.33 (30.15 to 30.50) |
| Unet + PatchGAN | 0.00173 (0.00164 to 0.00182) | 0.833 (0.831 to 0.835) | 29.95 (29.79 to 30.11) |
| Unet + ImageGAN | 0.00191 (0.00181 to 0.00201) | 0.833 (0.831 to 0.835) | 29.51 (29.35 to 29.68) |

TABLE 3

Full-Reference (FR) Image Quality metrics

Hepatic Angiograms (Dataset B)

| Method | MSE | SSIM | PSNR |
|---|---|---|---|
| Unet | 0.00365 (0.00337 to 0.00393) | 0.790 (0.781 to 0.800) | 26.02 (25.66 to 26.37) |
| Unet + PixelGAN | 0.00339 (0.00311 to 0.00367) | 0.805 (0.796 to 0.814) | 26.24 (25.92 to 26.56) |
| Unet + PatchGAN | 0.00331 (0.00304 to 0.00358) | 0.755 (0.746 to 0.764) | 26.22 (25.91 to 26.52) |
| Unet + ImageGAN | 0.00322 (0.00298 to 0.00346) | 0.746 (0.737 to 0.755) | 26.17 (25.87 to 26.46) |

TABLE 4

Full-Reference (FR) Image Quality metrics

Hepatic Angiograms (Dataset B)

| Method | MSE | SSIM | PSNR |
|---|---|---|---|
| Without Transfer Learning | 0.01630 (0.01429 to 0.01831) | 0.667 (0.66 to 0.673) | 20.27 (19.90 to 20.64) |
| With Transfer Learning | 0.00331 (0.00304 to 0.00358) | 0.755 (0.746 to 0.764) | 26.22 (25.91 to 26.52) |
| p-value | $<1 \times 10^{-5}$ | $<1 \times 10^{-5}$ | $<1 \times 10^{-5}$ |

Figure 5:
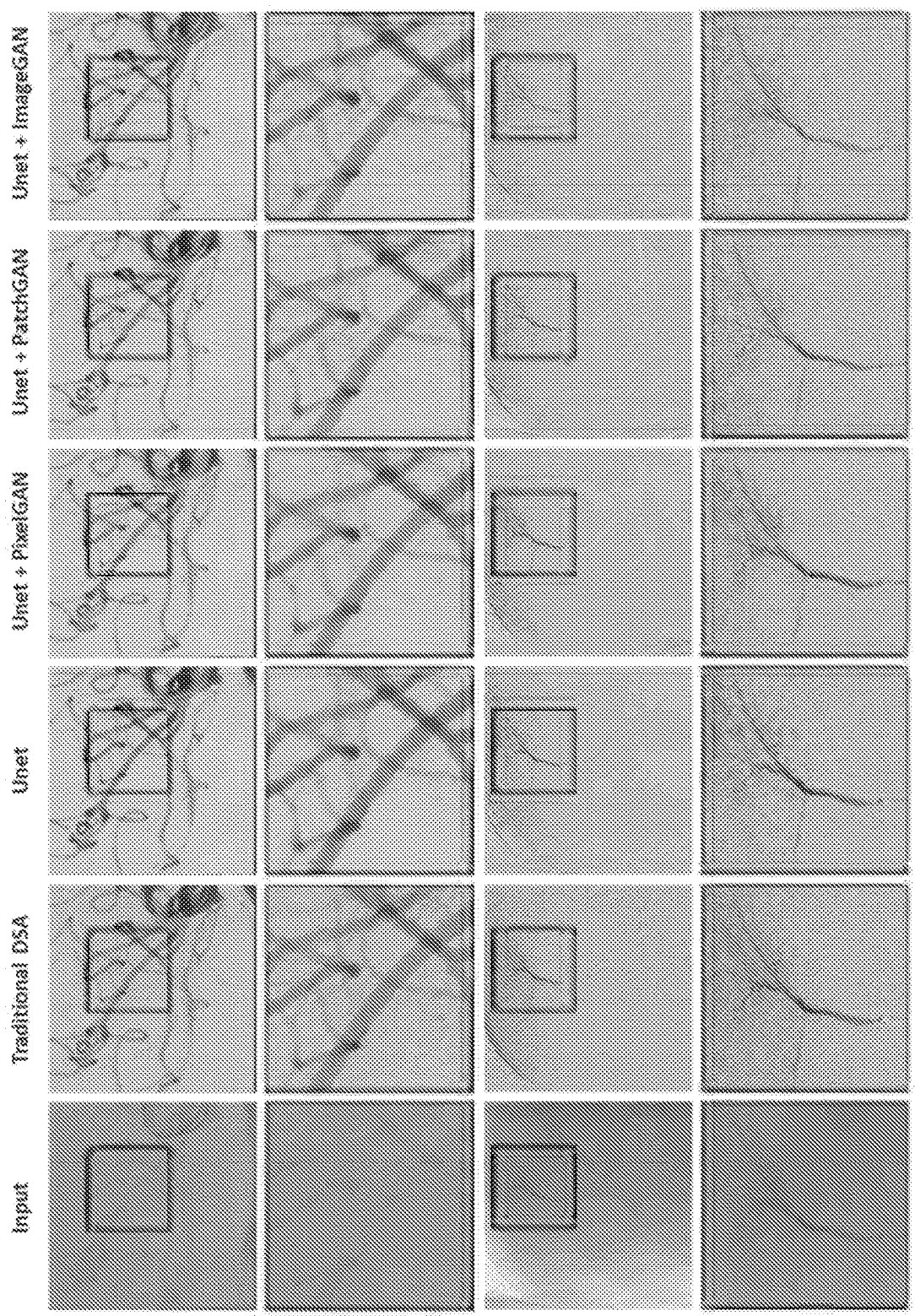
FIG. 5 illustrates image results for each algorithm combination trained on datasets A and B, the cerebral and hepatic angiograms respectively.

When performing the qualitative assessment, a visual review of generated images by the proposed methods for the cerebral and hepatic angiograms (datasets A and B) can be seen in FIG. 5. FIG. 5 illustrates image results for each algorithm combination trained on datasets A and B, the cerebral and hepatic angiograms respectively. The first column shows the fluoroscopic images used as inputs, the second column shows ground truth DSA images, and the third through sixth columns show outputs generated using each network architecture. For both the cerebral and hepatic angiograms, each network is able to accurately identify the vasculature of interest and reproduce the ground truth DSA images in the setting of no motion artifacts. However, the method Unet+PatchGAN shows the most consistent ability to sharply delineate the vasculature of interest.

Figure 6:
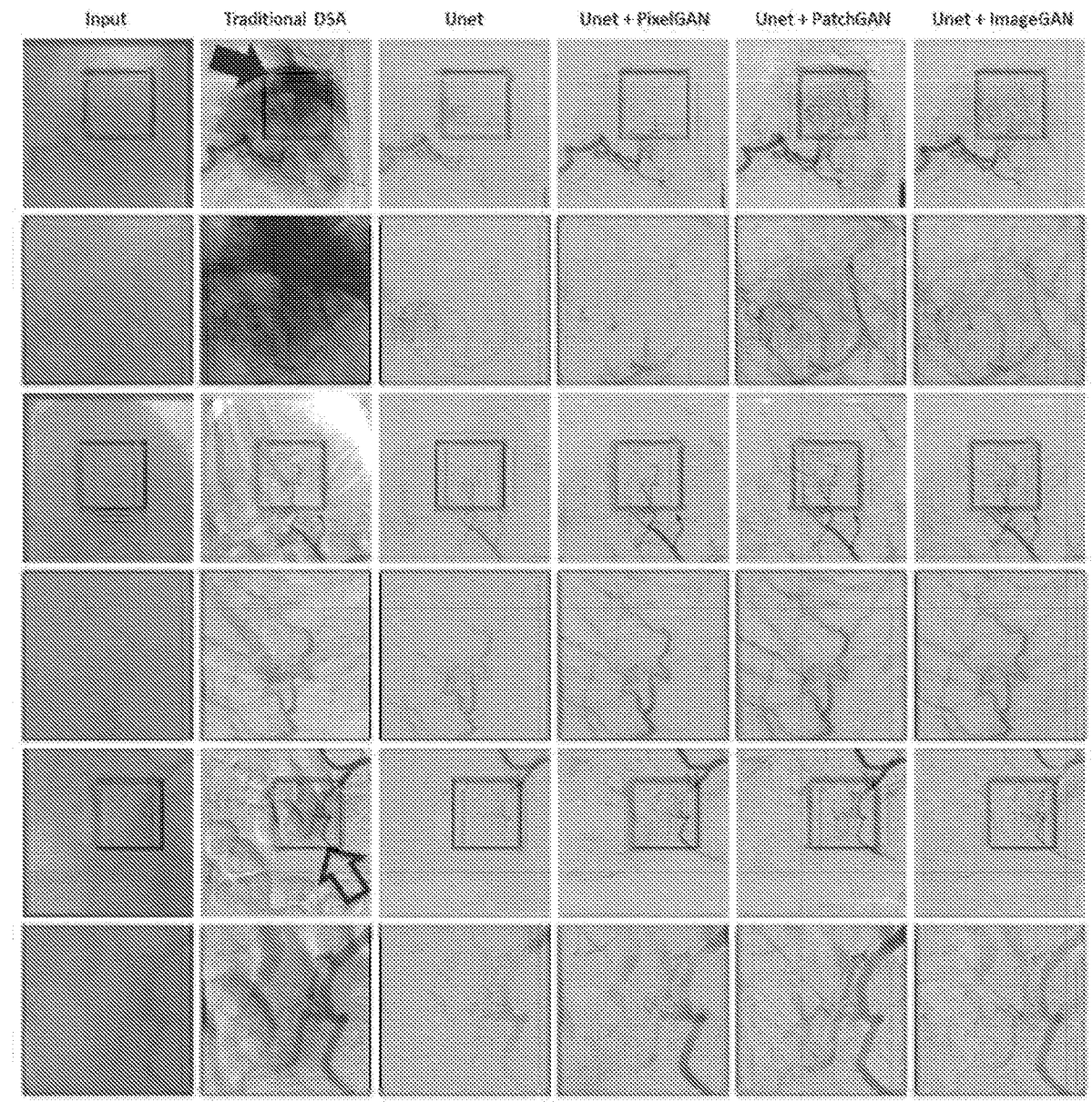
FIG. 6 illustrates image results for the fully trained algorithm combinations tested on dataset C, which contains visceral angiograms with significant motion artifacts.

Additionally, to assess the ability of the networks to reliably eliminate motion artifacts, a visual review of images generated from dataset C, the visceral angiograms containing significant motion artifacts, was performed. Representative examples from this visual review are shown in FIG. 6. FIG. 6 illustrates image results for the fully trained algorithm combinations tested on dataset C, which contains visceral angiograms with significant motion artifacts. The first column shows the fluoroscopic images used as inputs, the second column shows traditional DSA images, and the third through sixth columns show outputs generated using each network architecture. The generated images show successful suppression of motion artifacts that were present when using the traditional DSA method; furthermore, the method Unet+PatchGAN shows the most consistent ability to accurately identify the vasculature of interest.

Figure 7:
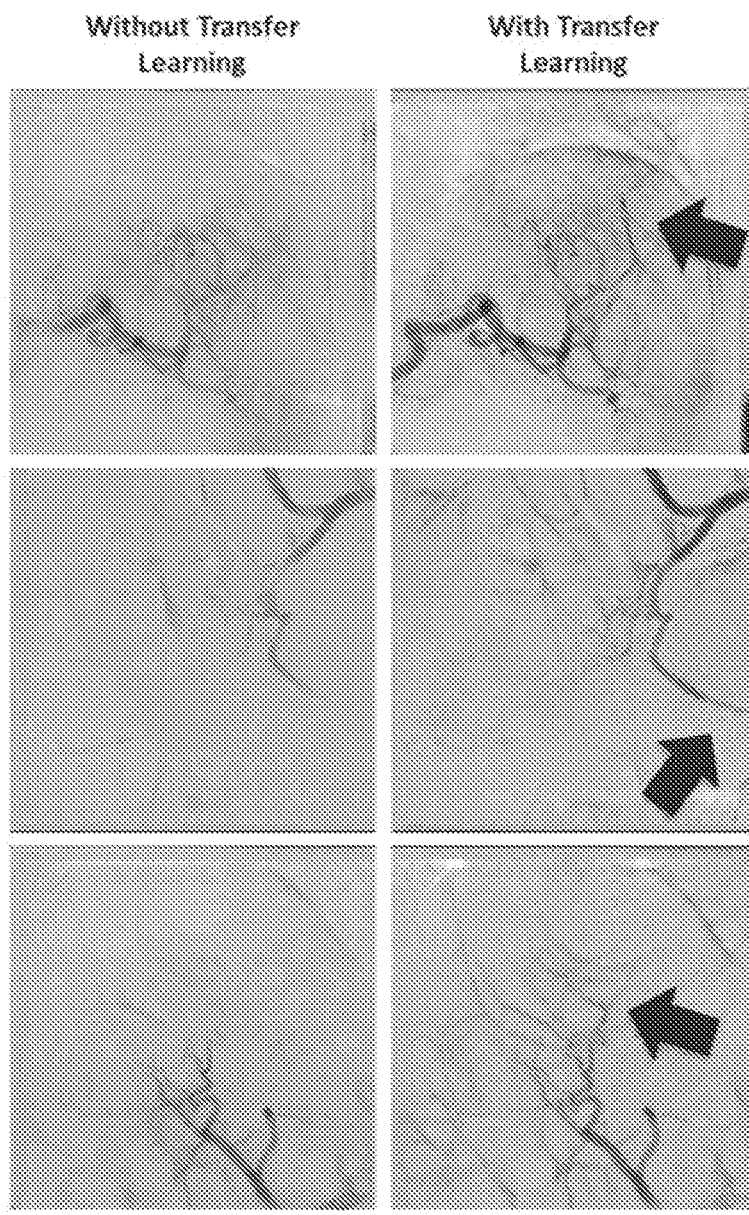
FIG. 7 illustrates a qualitative comparison of Unet+ PatchGAN performance on visceral angiograms with motion artifacts (dataset C), with and without transfer learning from cerebral angiograms (dataset A).

Additionally, a visual comparison of images generated from dataset C for the method Unet+PatchGAN, trained with and without transfer learning on dataset A (cerebral angiograms), can be seen in FIG. 7. FIG. 7 illustrates a qualitative comparison of Unet+PatchGAN performance on visceral angiograms with motion artifacts (dataset C), with and without transfer learning from cerebral angiograms (dataset A). Transfer learning from dataset A significantly improves the algorithm's ability to reliably eliminate motion artifacts from visceral angiograms and identify the vasculature of interest (solid arrows).

In at least one embodiment, DSA images generated using the Unet+PatchGAN architecture successfully suppress motion artifacts in visceral angiograms while also preserving critical structures such as the vasculature. By utilizing transfer learning, this technology can be applied to areas of the body, such as the viscera, where training data is critically limited. Furthermore, this motion correction is performed in near real time, with each 512×512 pixel image being processed in 0.023 seconds on average. In certain clinical circumstances, this approach already has the potential to aid in identifying the direction of a particular vessel that might otherwise be obscured by motion.

Further, the methods may be practiced by a computer system including one or more processors and computer-readable media such as computer memory. In particular, the computer memory may store computer-executable instructions that when executed by one or more processors cause various functions to be performed, such as the acts recited in the embodiments.

Computing system functionality can be enhanced by a computing systems' ability to be interconnected to other computing systems via network connections. Network connections may include, but are not limited to, connections via wired or wireless Ethernet, cellular connections, or even computer to computer connections through serial, parallel, USB, or other connections. The connections allow a computing system to access services at other computing systems and to quickly and efficiently receive application data from other computing systems.

Interconnection of computing systems has facilitated distributed computing systems, such as so-called "cloud" computing systems. In this description, "cloud computing" may be systems or resources for enabling ubiquitous, convenient, on-demand network access to a shared pool of configurable computing resources (e.g., networks, servers, storage, applications, services, etc.) that can be provisioned and released with reduced management effort or service provider interaction. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

Cloud and remote based service applications are prevalent. Such applications are hosted on public and private remote systems such as clouds and usually offer a set of web based services for communicating back and forth with clients.

Many computers are intended to be used by direct user interaction with the computer. As such, computers have input hardware and software user interfaces to facilitate user interaction. For example, a modern general purpose computer may include a keyboard, mouse, touchpad, camera, etc. for allowing a user to input data into the computer. In addition, various software user interfaces may be available.

Examples of software user interfaces include graphical user interfaces, text command line based user interface, function key or hot key user interfaces, and the like.

Disclosed embodiments may comprise or utilize a special purpose or general-purpose computer including computer hardware, as discussed in greater detail below. Disclosed embodiments also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: physical computer-readable storage media and transmission computer-readable media.

Physical computer-readable storage media includes RAM, ROM, EEPROM, CD-ROM or other optical disk storage (such as CDs, DVDs, etc.), magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry program code in the form of computer-executable instructions or data structures and which can be accessed by a general purpose or special purpose computer. Combinations of the above are also included within the scope of computer-readable media.

Further, upon reaching various computer system components, program code means in the form of computer-executable instructions or data structures that can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A computer system for removing motion artifacts in medical images using a generative adversarial network (GAN) comprising:

one or more processors; and
one or more computer-readable media having stored thereon executable instructions that when executed by the one or more processors configure the computer system to perform at least the following:
instantiate the generative adversarial network (GAN) having one or more generative network(s) and one or more discriminative network(s) that are pitted against each other to train a generative model and a discriminative model,
wherein the training of the generative network(s) and the discriminative network(s) uses a training dataset comprising a first plurality of medical images that are previously classified as without significant motion artifacts for diagnostic purposes;
wherein the discriminative model is trained to classify medical images as artificially generated or real; and
wherein the generative model is trained to enhance the quality of a medical image and remove motion artifacts by producing an image without the use of a pre-contrast mask.

2. The computer system of claim 1, the computer system further configured to:
receive a new medical image having significant motion artifacts; and
enhance quality of the new medical image by the generative model, such that the enhanced medical image no longer has significant motion artifacts.

3. The computer system of claim 2, the computer system further configured to:
determine whether the new medical image has significant motion artifacts; and
in response to the determination of having significant motion artifacts, cause the generative model to enhance the first medical image by substantially removing the motion artifacts in the new medical image.

4. The computer system of claim 1, the computer system further configured to modify the discriminative model and generative model by transfer learning, comprising:
continue to train the previously trained discriminative model and the generative model using a second plurality of medical images that are different from the first plurality of medical images, wherein the second plurality of medical images are also previously classified as without significant motion artifacts.

5. The computer system of claim 1, the computer system further configured to:
for each of the first plurality of medical images, when the medical image is not with a predetermined size, transform the image into one or more images of the predetermined size; and
use the medical images having the predetermined size as the training dataset.

6. The computer system of claim 5, wherein for each of the plurality of images, when the image is greater than the predetermined size, split the image into a plurality of images having the predetermined size.

7. The computer system of claim 1, wherein the training dataset includes a plurality of medical images that have been confirmed by human experts as without significant motion artifacts.

8. The computer system of claim 5, the computer system further configured to:
receive a medical image having significant motion artifacts; and
cause the generative model to enhance quality of the medical image by substantially removing the motion artifacts, such that the enhanced medical image no longer has significant motion artifacts.

9. The computer system of claim 5, the computer system further configured to:
receive a contrast image prior to subtraction of a pre-contrast image; and
enhance the contrast image without having to subtract a pre-contrast image, such that the discriminative model classifies the enhanced image as a real medical image without significant motion artifact.

10. The computer system of claim 1, wherein each of the one or more discriminative network(s) is a convolutional network.

11. The computer system of claim 10, wherein each of the convolutional network(s) includes a receptive field having a predetermined size.

12. The computer system of claim 11, wherein a size of a receptive field of each of the convolutional network(s) is selective from 1×1, 70×70, or 286×286.

13. The computer system of claim 10, wherein at least one of the convolutional network(s) includes U-Net convolutional network(s).

14. The computer system of claim 1, wherein:
the GAN has an objective represented by an objective function,
the discriminative network(s) is configured to maximize the objective; and
the generative network(s) is configured to minimize the objective.

15. The computer system of claim 14, wherein the objective includes a distance loss.

16. The computer system of claim 14, wherein the objective includes a distance loss plus an adversarial loss.

17. The computer system of claim 1, wherein the GAN is one of the following: (1) pixelGAN, (2) patchGAN, or (3) imageGAN.

18. The computer system of claim 17, wherein the GAN is a patchGAN, in which the discriminative network classifies a digital medical image as real or artificial when each patch having a predetermined size in the digital medical image has no significant motion artifacts.

19. A method for removing motion artifacts in medical images using a generative adversarial network, the method comprising:
instantiating the generative adversarial network (GAN) having one or more generative network(s) and one or more discriminative network(s) that are pitted against each other to train a generative model and a discriminative model,
wherein the training of the generative network(s) and the discriminative network(s) uses a training dataset comprising a first plurality of medical images that are previously classified as without significant motion artifacts for diagnostic purposes;
wherein the discriminative model is trained to classify medical images as artificially generated or real; and
wherein the generative model is trained to enhance the quality of a medical image and remove motion artifacts by producing an image without the use of a pre-contrast mask.

20. The method of claim 19, further comprising:
receive a first medical image having significant motion artifacts; and
enhance quality of the first medical image by the generative model, such that the enhanced medical image no longer has significant motion artifacts.

* * * * *